United States Patent
El-Khatib et al.

(10) Patent No.: US 12,280,241 B2
(45) Date of Patent: Apr. 22, 2025

(54) GLUCOSE CONTROL SYSTEM WITH AUTOMATIC ADAPTATION OF GLUCOSE TARGET

(71) Applicants: Trustees of Boston University, Boston, MA (US); The General Hospital Corporation, Boston, MA (US)

(72) Inventors: Firas H. El-Khatib, Allston, MA (US); Edward R. Damiano, Acton, MA (US); Steven J. Russell, Lincoln, MA (US)

(73) Assignees: Trustees of Boston University, Boston, MA (US); The General Hospital Corporation, Boston, MA (US)

( * ) Notice: Subject to any disclaimer, the term of this patent is extended or adjusted under 35 U.S.C. 154(b) by 11 days.

(21) Appl. No.: 18/223,315

(22) Filed: Jul. 18, 2023

(65) Prior Publication Data

US 2024/0165327 A1     May 23, 2024

Related U.S. Application Data

(63) Continuation of application No. 17/099,126, filed on Nov. 16, 2020, now Pat. No. 11,744,945, which is a
(Continued)

(51) Int. Cl.
    *A61M 5/172*         (2006.01)
    *A61B 5/00*          (2006.01)
    (Continued)

(52) U.S. Cl.
    CPC ....... *A61M 5/1723* (2013.01); *A61B 5/14532* (2013.01); *A61B 5/4839* (2013.01); *A61M 2005/14208* (2013.01)

(58) Field of Classification Search
    CPC ............. A61B 5/14532; A61B 5/4839; A61M 5/1723; A61M 2005/14208
See application file for complete search history.

(56) References Cited

U.S. PATENT DOCUMENTS

| | | |
|---|---|---|
| 4,280,494 A | 7/1981 | Cosgrove et al. |
| 4,464,170 A | 8/1984 | Clemens et al. |
| (Continued) | | |

FOREIGN PATENT DOCUMENTS

| | | |
|---|---|---|
| CN | 1973768 | 6/2007 |
| CN | 201186082 | 1/2009 |
| (Continued) | | |

OTHER PUBLICATIONS

US 10,973,979 B2, 04/2021, El-Khatib (withdrawn)
(Continued)

*Primary Examiner* — Bradley J Osinski
(74) *Attorney, Agent, or Firm* — BainwoodHuang

(57) ABSTRACT

A glucose control system employs adaptation of a glucose target (set-point) control variable in controlling delivery of insulin to a subject to maintain euglycemia. The glucose target adapts based on trends in actual glucose level (e.g., measured blood glucose in the subject), and/or computed doses of a counter-regulatory agent such as glucagon. An adaptation region with upper and lower bounds for the glucose target may be imposed. Generally the disclosed techniques can provide for robust and safe glucose level control. Adaptation may be based on computed doses of a counter-regulatory agent whether or not such agent is actually delivered to the subject, and may be used for example to adjust operation in a bihormonal system during periods in which the counter-regulatory agent is not available for delivery.

19 Claims, 5 Drawing Sheets

Related U.S. Application Data continuation of application No. 15/748,333, filed as application No. PCT/US2016/046008 on Aug. 8, 2016, now Pat. No. 10,842,934.

(60) Provisional application No. 62/202,505, filed on Aug. 7, 2015.

(51) Int. Cl.
*A61B 5/145* (2006.01)
*A61M 5/142* (2006.01)

(56) References Cited

U.S. PATENT DOCUMENTS

| | | |
|---|---|---|
| 5,665,065 A | 9/1997 | Colman |
| 6,544,212 B2 | 4/2003 | Galley et al. |
| 6,554,798 B1 | 4/2003 | Mann et al. |
| 6,572,542 B1 | 6/2003 | Houben |
| 7,347,836 B2 | 3/2008 | Peterson |
| 7,491,187 B2 | 2/2009 | Van Den Berghe et al. |
| 7,651,845 B2 | 1/2010 | Doyle, III et al. |
| 7,655,618 B2 | 2/2010 | Green et al. |
| 7,678,762 B2 | 3/2010 | Green et al. |
| 7,678,763 B2 | 3/2010 | Green et al. |
| 7,683,027 B2 | 3/2010 | Green et al. |
| 7,766,829 B2 | 8/2010 | Sloan et al. |
| 7,806,854 B2 | 10/2010 | Damiano et al. |
| 7,850,641 B2 | 12/2010 | Lebel et al. |
| 8,273,052 B2 | 9/2012 | Damiano et al. |
| 8,348,842 B1 | 1/2013 | Osorio |
| 8,377,031 B2 | 2/2013 | Hayter et al. |
| 8,454,510 B2 | 6/2013 | Yodfat et al. |
| 8,457,901 B2 | 6/2013 | Beshan |
| 8,478,557 B2 | 7/2013 | Hayter |
| 8,562,587 B2 | 10/2013 | Kovatchev et al. |
| 8,622,988 B2 | 1/2014 | Hayter |
| 8,679,016 B2 | 3/2014 | Mastrototaro et al. |
| 8,690,820 B2 | 4/2014 | Cinar |
| 8,840,582 B2 | 9/2014 | Blomquist et al. |
| 9,283,323 B2 | 3/2016 | Toumazou |
| 9,351,670 B2 | 5/2016 | Dunn |
| 9,398,869 B2 | 7/2016 | Kovatchev et al. |
| 9,445,757 B2 | 9/2016 | Desborough |
| 9,486,578 B2 | 11/2016 | Finan |
| 9,750,438 B2 | 9/2017 | Kovatchev et al. |
| 9,833,570 B2 | 12/2017 | El-Khatib et al. |
| 9,839,395 B2 | 12/2017 | Shariati |
| 9,901,677 B2 | 2/2018 | Estes |
| 9,907,909 B2 | 3/2018 | Finan |
| 9,999,728 B2 | 6/2018 | Parikh |
| 10,188,793 B2 | 1/2019 | Mazlish |
| 10,357,607 B2 | 7/2019 | Blomquist et al. |
| 10,463,786 B2 | 11/2019 | Saint |
| 10,543,313 B2 | 1/2020 | Damiano et al. |
| 10,569,016 B2 | 2/2020 | Rosinko |
| 10,653,834 B2 | 5/2020 | Kruse et al. |
| 10,842,934 B2 | 11/2020 | El-Khatib et al. |
| 10,887,795 B2 | 1/2021 | Deparisse |
| 10,940,267 B2 | 3/2021 | El-Khatib |
| 10,960,137 B2 | 3/2021 | El-Khatib et al. |
| 2003/0181852 A1 | 9/2003 | Mann et al. |
| 2004/0028707 A1 | 2/2004 | Pinkerton |
| 2004/0034295 A1 | 2/2004 | Salganicoff |
| 2004/0147872 A1 | 7/2004 | Thompson |
| 2004/0253736 A1 | 12/2004 | Stout et al. |
| 2005/0182366 A1 | 8/2005 | Vogt et al. |
| 2005/0272640 A1 | 12/2005 | Doyle, III et al. |
| 2006/0272652 A1 | 12/2006 | Stocker |
| 2006/0276771 A1 | 12/2006 | Gally |
| 2007/0255348 A1 | 11/2007 | Holtzclaw |
| 2007/0282299 A1 | 12/2007 | Hellwig |
| 2008/0154187 A1 | 6/2008 | Krulevitch |
| 2008/0183060 A1 | 7/2008 | Steil et al. |
| 2008/0208113 A1 | 8/2008 | Damiano et al. |
| 2008/0269714 A1 | 10/2008 | Mastrototaro |
| 2008/0319384 A1 | 12/2008 | Yodfat et al. |
| 2009/0006061 A1 | 1/2009 | Thukral et al. |
| 2009/0036753 A1 | 2/2009 | King |
| 2009/0164239 A1 | 6/2009 | Hayter et al. |
| 2009/0177154 A1 | 7/2009 | Blomquist |
| 2010/0057057 A1 | 3/2010 | Hayter et al. |
| 2010/0082167 A1 | 4/2010 | Haueter |
| 2010/0125241 A1 | 5/2010 | Prud'Homme et al. |
| 2010/0137788 A1 | 6/2010 | Braithwaite et al. |
| 2010/0145262 A1 | 6/2010 | Bengtsson |
| 2010/0256466 A1 | 10/2010 | Shekalim |
| 2010/0262117 A1 | 10/2010 | Magni et al. |
| 2010/0292634 A1 | 11/2010 | Kircher, Jr. |
| 2011/0021898 A1 | 1/2011 | Wei et al. |
| 2011/0054391 A1 | 3/2011 | Ward et al. |
| 2011/0098638 A1 | 4/2011 | Chawla |
| 2011/0208155 A1 | 8/2011 | Palerm et al. |
| 2011/0208156 A1 | 8/2011 | Doyle, III et al. |
| 2011/0218489 A1 | 9/2011 | Mastrototaro et al. |
| 2012/0065894 A1 | 3/2012 | Tubb et al. |
| 2012/0078067 A1 | 3/2012 | Kovatchev et al. |
| 2012/0245556 A1 | 9/2012 | Kovatchev et al. |
| 2012/0246106 A1 | 9/2012 | Atlas et al. |
| 2012/0265126 A1 | 10/2012 | Estes |
| 2012/0265722 A1 | 10/2012 | Blomquist |
| 2012/0277723 A1 | 11/2012 | Skladnev |
| 2012/0283694 A1 | 11/2012 | Yodfat et al. |
| 2013/0190583 A1 | 7/2013 | Grosman |
| 2014/0031786 A1 | 1/2014 | Kircher, Jr. et al. |
| 2014/0276555 A1 | 9/2014 | Morales |
| 2015/0018633 A1 | 1/2015 | Kovachev et al. |
| 2015/0151050 A1 | 6/2015 | Estes |
| 2015/0217052 A1 | 8/2015 | Keenan et al. |
| 2015/0217053 A1 | 8/2015 | Booth |
| 2016/0224751 A1 | 8/2016 | Bielawa |
| 2016/0224756 A1 | 8/2016 | Berger |
| 2016/0331898 A1 | 11/2016 | Damiano |
| 2017/0095612 A1 | 4/2017 | El-Khatib et al. |
| 2017/0136198 A1 | 5/2017 | Delangre et al. |
| 2017/0203038 A1 | 7/2017 | Desborough et al. |
| 2018/0021514 A1 | 1/2018 | Rosinko |
| 2018/0103897 A1 | 4/2018 | Amirouche |
| 2018/0133398 A1 | 5/2018 | Blomquist |
| 2018/0185587 A1 | 7/2018 | Brauker |
| 2018/0200440 A1 | 7/2018 | Mazlish et al. |
| 2018/0296757 A1 | 10/2018 | Finan |
| 2019/0214124 A1 | 7/2019 | Mougiakakou |
| 2019/0247578 A1 | 8/2019 | Desborough et al. |
| 2019/0336684 A1 | 11/2019 | O'Connor |
| 2020/0254240 A1 | 8/2020 | Windmiller |
| 2020/0384190 A1 | 12/2020 | Jacobi |
| 2021/0085869 A1 | 3/2021 | El-Khatib et al. |
| 2021/0213200 A1 | 7/2021 | Raskin et al. |

FOREIGN PATENT DOCUMENTS

| | | |
|---|---|---|
| CN | 101795623 | 8/2010 |
| CN | 102667787 | 9/2012 |
| CN | 104667368 | 8/2017 |
| CN | 104667379 | 8/2017 |
| EP | 1 575 656 | 6/2009 |
| EP | 3 453 414 | 3/2019 |
| JP | 03-500129 | 3/1989 |
| JP | 2001-204817 | 7/2001 |
| JP | 2003-079723 | 3/2003 |
| JP | 2004-502474 | 1/2004 |
| JP | 2007-529241 | 10/2007 |
| JP | 2007-312923 | 12/2007 |
| JP | 2012-516735 | 7/2012 |
| JP | 2012-519018 | 8/2012 |
| WO | WO 04/006982 | 1/2004 |
| WO | WO 04/084820 | 10/2004 |
| WO | WO 06/124716 | 11/2006 |
| WO | WO 08/057384 | 5/2008 |
| WO | WO 08/094249 | 8/2008 |
| WO | WO 08/114254 | 9/2008 |
| WO | WO 08/157780 | 12/2008 |
| WO | WO 09/001349 | 12/2008 |

(56) References Cited

FOREIGN PATENT DOCUMENTS

| WO | WO 12/058694 | 5/2012 |
|----|--------------|--------|
| WO | WO 14/110541 | 7/2014 |
| WO | WO 15/021041 | 2/2015 |

OTHER PUBLICATIONS

El-Khatib et al., Apr. 14, 2010, A Bihormonal Closed-Loop Artificial Pancreas for Type 1 Diabetes, Science. Trans. Med., 2(27):1-12.
El-Khatib et al., Jul. 2009, A Feasibility Study of Bihormonal Closed-Loop Blood-Glucose Control Using Dual Subcutaneous Infusion of Insulin and Glucagon in Ambulatory Diabetic Swine, Journal of Diabetes Science and Technology, 3(4):789-803.
El-Khatib, et al., Mar. 2007, Adaptive Closed-Loop Control Provides Blood-Glucose Regulation Using Dual Subcutaneous Insulin and Glucagon Infusion in Diabetic Swine, Journal of Diabetes Science and Technology, 1(2):181-192.
El-Khatib, et al., May 2014, Autonomous and Continuous Adaptation of a Bihormonal Bionic Pancreas in Adults and Adolescents Nilh Type 1 Diabetes, Journal of Clinical Endocrin. Melab., 99(5):1701-1711.
Russell, et al., Jun. 15, 2014, Outpatient Glycemic Control with a Bionic Pancreas in Type 1 Diabetes, The New England Journal of Medicine, 371(4):313-325.
Russell, et al., Nov. 2012, Blood Glucose Control in Type 1 Diabetes With a Bihormonal Bionic Endocrine Pancreas, Diabetes Care, 35:2148-2155.
Albisser et al., May 1974, An Artificial Endocrine Pancreas, Diabetes, 23(5):389-396.
Bellazzi et al., 1995, Adaptive Controllers for Intelligent Monitoring, Artif. Intell. Med., 7:515-540.
Bellomo et al., May 1982, Optimal Feedback Glycaemia Regulation in Diabetics, Med. & Biol. Eng. & Comp. 20:329-335.
Berian et al., 2019, A wearable closed-loop insulin delivery system based on low-power SoCs, Electronics, 8:612.
Botz, May 1976, An Improved Control Algorithm for an Artificial .beta.-Cell, IEEE Trans. Biomed. Eng., BME-23(3):252-255.
Brunetti et al., 1993, A Simulation Study on a Self-Tuning Portable Controller of Blood Glucose, Int. J. Artif. Org., 16(1):51-57.
Candas et al., Feb. 1994, An Adaptive Plasma Glucose Controller Based on a Nonlinear Insulin/Glucose Model, IEEE Trans. Biomed. Eng. 41(2):116-124.
Clarke et al., 2009, Statistical Tools to Analyze Continuous Glucose Monitor Data, Diabetes Technology and Therapeutics, 11:S45-S54.
Clemens, 1979, Feedback Control Dynamics for Glucose Controlled Insulin Infusion Systems, Med. Prog. Technol. 6:91-98.
Femat et al., Aug. 22-27, 1999, Blood Glucose Regulation: An Output Feedback Approach, Proc. IEEE Int. Conf. Control App. pp. 1290-1293.
Fischer et al., Aug. 1987, Does Physiological Blood Glucose Control Require an Adaptive Control Strategy?, IEEE Trans. Biomed. Eng., BME-34:575-582.
Fletcher et al., 2001, Feasibility of an Implanted, Closed-Loop, Blood-Glucose Control Device, Immunology 230, Stanford University, Spring 01, 31 pp.
Furler et al., Nov.-Dec. 1985, Blood Glucose Control by Intermittent Loop Closure in the Basal Mode: Computer Simulation Studies with a Diabetic Model, Diabetes Care, 8(6):553-561.
Kan et al., 2000, Novel Control System for Blood Glucose Using a Model Predictive Method, ASAIO Journal, 4:657-662.
Lal et al., Jul. 5, 2019, Realizing a closed-loop (artificial pancreas) system for the treatment of type 1 diabetes, Endocrine reviews, 40(6):1521-1546.
Lauritzen et al., May 1983 Pharmacokinetics of Continuous Subcutaneous Insulin Infusion, Diabetologia, 24(5):326-329.
Marliss et al., Jul. 1977, Normalization of Glycemia in Diabetics During Meals with Insulin and Glucagon Delivery by the Artificial Pancreas, Diabetes, 26:663-672.
Medtronic, 2020, Minimed™ 670G Insulin Pump System, product brochure, https://www.medtronicdiabetes.com/products/minimed-670g-insulin-pump-system, 7 pp.
Pagurek et al., 1972, Adaptive Control of the Human Glucose Regulatory System, Med. Biol. Eng., 10:752-761.
Panteleon et al., Jul. 2006, Evaluation of the effect of gain on the meal response of an automated closed-loop insulin delivery system, Diabetes, 55:1995-2000.
Parker et al., 1996, Model Predictive Control for Infusion Pump Insulin Delivery, Proceedings of the 18th Annual International Conference of the IEEE, 6:1822-1823.
Parker et al., Feb. 1999, A Model-Based Algorithm for Blood Glucose Control in Type 1 Diabetic Patients, IEEE Trans. Biomed. Eng. 46(2):148-157.
Parker et al., Jan.-Feb. 2001, The Intravenous Route to Blood Glucose Control, IEEE Eng. Med. & Biol., pp. 65-73.
Parrish et al., Jun. 1997, Control of an Artificial Human Pancreas Using the SDRE Method, Proc. American Control Conf., 2:1059-1060.
Russell et al., Nov. 2010, Efficacy Determinants of Subcutaneous Microdose Glucagon during Closed-Loop Control, Journal of Diabetes Science and Technology, 4(6):1288-1304.
Sivaramakrishnan et al., 2017, Optimal model based control for blood glucose insulin system using continuous glucose monitoring, J. Pharm. Sci & Res., 9(4):465-469.
Steil et al., 2006, Metabolic modelling and the closed-loop insulin delivery problem, Diabetes Research and Clinical Practice, 74:S183-S186.
Steil et al., Dec. 2006, Feasibility of automating insulin delivery for the treatment of type 1 diabetes, Diabetes, 55:3344-3350.
Trajanoski et al., Sep. 1998, Neural Predictive Controller for Insulin Delivery Using the Subcutaneous Route, Biomedical Engineering, 45(9):1122-1134.
University of California, San Francisco, Diabetes Education Online, Calculating Insulin Dose, https://dtc.ucsf.edu/types-of-diabetes/type2/treatment-of-type-2-diabetes/medications-and-therapies/type-2-insulin-rx/calculating-insulin-dose/, downloaded Apr. 9, 2021, 11 pp.
International Search Report and Written Opinion dated Oct. 21, 2016 in application No. PCT/US16/46008.

GLUCOSE CONTROL SYSTEM WITH AUTOMATIC ADAPTATION OF GLUCOSE TARGET

STATEMENT OF GOVERNMENT RIGHTS

This invention was made with US Government support under contracts DK097657 and DK101084 awarded by the National Institutes of Health. The Government has certain rights in the invention.

BACKGROUND

The present invention is related to the field of medical systems and devices, and more specifically to medical systems and devices for controlling delivery of insulin (including analogs) to a subject to maintain euglycemia.

SUMMARY

Techniques are disclosed for adaptation of a glucose target (set-point) control variable in a glucose control system controlling delivery of insulin to a subject to maintain euglycemia, e.g., a blood-glucose control system. In this description the term "insulin" encompasses all forms of insulin-like substances including natural human or animal insulin as well as synthetic insulin in any of a variety of forms (commonly referred to as an "insulin analogs"). Generally, the glucose target adapts based on trends in actual glucose level (e.g., measured blood glucose in the subject), and/or computed doses of a counter-regulatory agent (e.g. glucagon or dextrose). An adaptation region with upper and lower bounds for the glucose target may be imposed. The disclosed techniques can provide for robust and safe glucose level control. In one embodiment, adaptation is based on computed doses of a counter-regulatory agent whether or not such agent is available or actually delivered to the subject, and may be used for example to adjust operation in a bihormonal control system, including during periods in which the counter-regulatory agent is not available for delivery, or in an insulin-only control system where (hypothetical) doses of a counter-regulatory agent are computed even it is absent. Alternatively, adaptation can be based on trends in glucose level (including emphasis on the extent and/or duration of low glucose levels or trends and/or the mean glucose) or a combination of trends in glucose level and computed doses of a counter-regulatory agent.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views.

DETAILED DESCRIPTION

Overview

Figure 1:
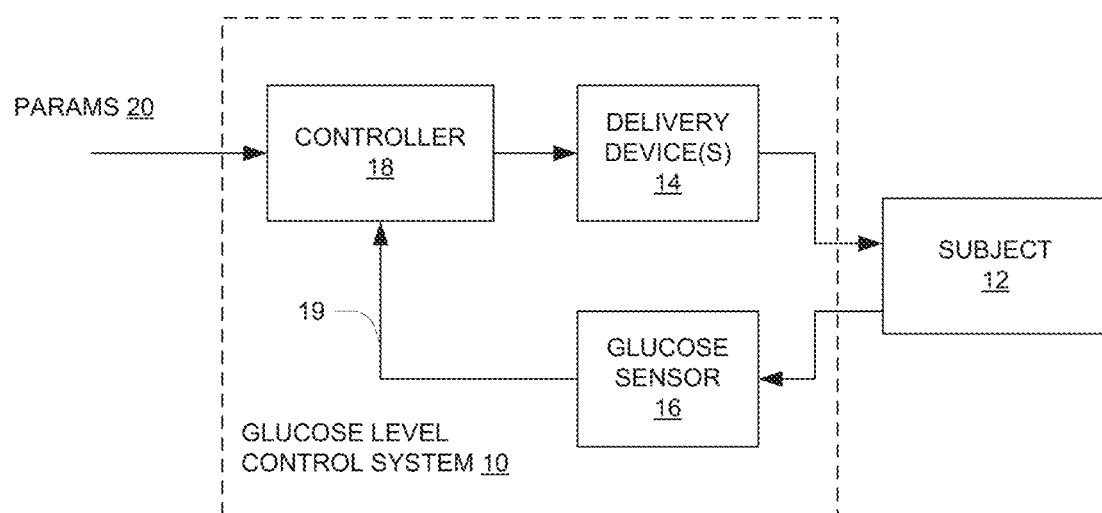
FIG. 1 is a block diagram of a blood glucose level control system.

A technique is described for automatically modulating the glucose target (set-point) used in an autonomous glucose-control system, whether employing the delivery of only insulin or the delivery of insulin as well as a counter-regulatory agent (e.g. glucagon or dextrose). The glucose target automatically adapts based on (a) the usage of a counter-regulatory agent, (b) the otherwise intended usage of a counter-regulatory agent had it been available (e.g. in insulin-only systems or in cases where the counter-regulatory agent or its delivery channel are temporarily unavailable), (c) trends in glucose level (including emphasis on the extent and/or duration of low glucose levels or trends and/or the mean glucose), or (d) any combination of these measures. The method may impose upper and/or lower bounds (static or dynamic) for the range over which the dynamic glucose target varies, and may coexist with an option for a user to set a static target on a temporary (including isolated, recurring, or scheduled) basis. The method can be implemented within an autonomous glucose-control system or during periods of autonomous control in a semi-autonomous glucose-control system.

An implementation example is in an automated insulin delivery system for ambulatory diabetes care. In such a system, the glucose target is set to float dynamically online, between lower and upper bounds, depending on the degree of hypoglycemia or near-hypoglycemia that the system records in a moving receding time window. The degree or rate at which the glucose target adapts either upwards (towards its upper bound) or downwards (towards its lower bound) for a given degree of hypoglycemia or near-hypoglycemia may be controlled by a system setting or scaling factor. For example, the higher the setting or scaling factor is, the more the glucose target will automatically rise for a given recorded degree of hypoglycemia or near hypoglycemia, and likewise fall as the degree of hypoglycemia decreases. Alternatively or additionally, the glucose target may be set to float dynamically online, between lower and upper bounds, depending on the degree to which the mean glucose level in a moving receding time window is outside a targeted range of mean glucose level values that are desired. For example, the system dynamically raises the glucose target if the mean glucose level is below a certain threshold, below which there is no predicted benefit of additional glucose lowering, even if the target might not otherwise be raised based on the degree of hypoglycemia.

In another implementation the glucose target floats dynamically based on computed counter-regulatory doses over a moving receding time window. The method may work identically whether the system is functioning in a multi-hormonal configuration, where the counter-regulatory doses are computed and their delivery is performed or at least intended or attempted as part of the system operation, or in an insulin-only configuration, where the counter-regulatory doses are computed only hypothetically (as if a counter-regulatory agent were available) but are not actually delivered. In either case, as online computed glucagon doses increase, the system automatically responds online by dynamically raising the glucose target. Moreover, the degree or rate at which the glucose target floats upwards (departing from its lower bound and towards its upper bound) for a given amount of computed glucagon doses may be controlled by a system setting or scaling factor. For example, the higher the setting or scaling factor is, the more the glucose target will automatically rise for a given computed glucagon dosing amount.

More Detailed Description

FIG. 1 illustrates an automated control system 10 for regulating the blood glucose level of an animal subject (subject) 12, which may be a human. The subject 12 receives doses of insulin from one or more delivery devices 14, for example infusion pump(s) coupled by catheter(s) to a subcutaneous space of the subject 12. As described below, the delivery devices 14 may also deliver a counter-regulatory agent such as glucagon for control of blood glucose level under certain circumstances. For the delivery of both insulin and glucagon, the delivery devices 14 may be mechanically driven infusion mechanisms having dual cartridges for insulin and glucagon respectively. In the present description, reference is made to glucagon specifically, but it is to be understood that this is for convenience only and that other counter-regulatory agents may be used. Similarly, the term "insulin" herein is to be understood as encompassing all forms of insulin-like substances including natural human or animal insulin as well as synthetic insulin in any of a variety of forms (commonly referred to as an "insulin analogs").

A glucose sensor 16 is operatively coupled to the subject 12 to continually sample a glucose level of the subject 12. Sensing may be accomplished in a variety of ways. A controller 18 controls operation of the delivery device(s) 14 as a function of a glucose level signal 19 from the glucose sensor 16 and subject to programmed input parameters (PARAMS) 20 which may be provided by the patient/user. One externally provided parameter is a "setpoint" which establishes a target blood glucose level that the system 10 strives to maintain. In the description below the externally provided setpoint is referred to as a "raw" target glucose level signal, and identified as "$r_t$". Generally the controller 18 operates based on a difference between a glucose level of the subject, as represented by the glucose level signal 19, and a target glucose level signal. As described more below, the raw target glucose level signal $r_t$ is one input to the calculation of a variable target glucose level signal that is used in calculating corrective doses and that represents certain adaptation of the control operation to achieve certain results.

The controller 18 is an electrical device with control circuitry that provides operating functionality as described herein. In one embodiment, the controller 18 may be realized as a computerized device having computer instruction processing circuitry that executes one or more computer programs each including respective sets of computer instructions. In this case the processing circuitry generally includes one or more processors along with memory and input/output circuitry coupled to the processor(s), where the memory stores computer program instructions and data and the input/output circuitry provides interface(s) to external devices such as the glucose sensor 16 and delivery device(s) 14.

Figure 2:
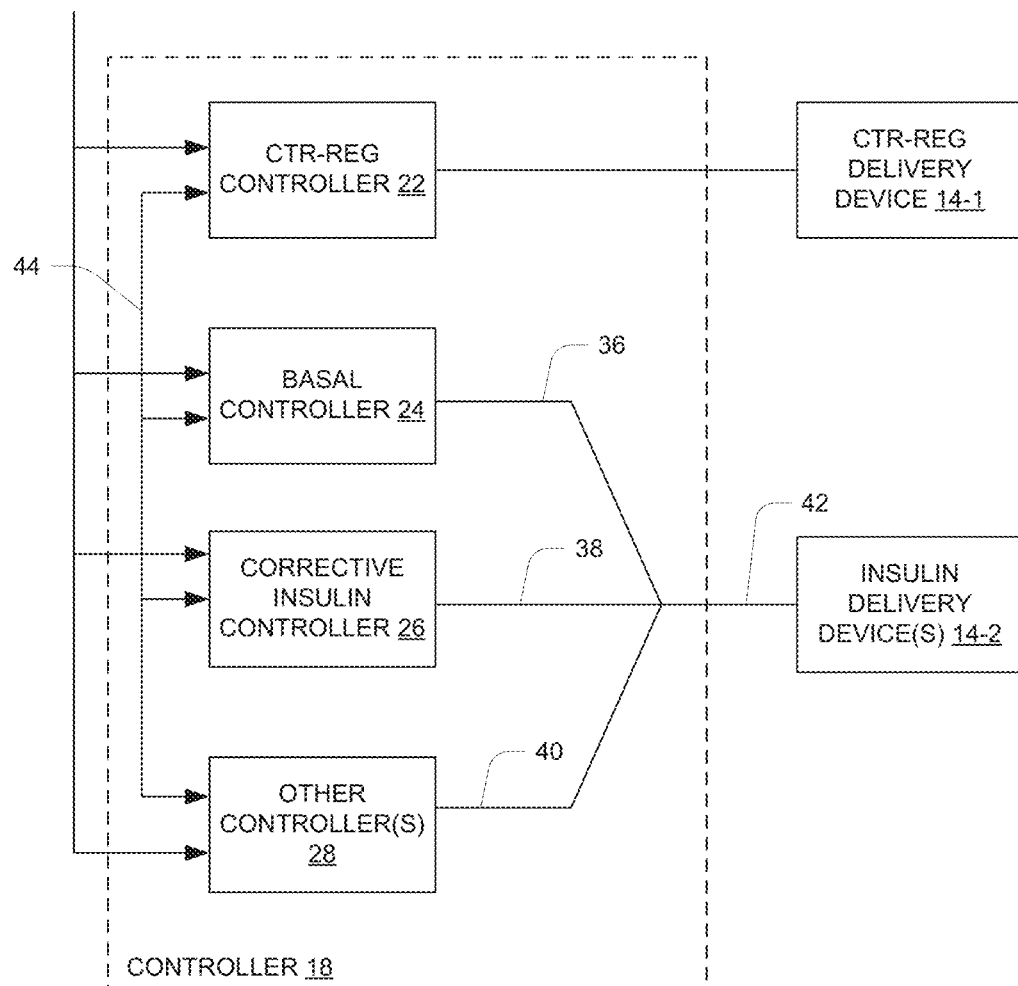
FIG. 2 is a block diagram of a blood glucose level controller.

FIG. 2 shows the functional structure of the controller 18. It includes four separate controllers, namely a counter-regulatory (CTR-REG) controller 22, basal insulin controller 24, corrective insulin controller 26. and other controller(s) 28. Each controller may be realized as a computerized device executing respective computer programs (i.e., counter-regulatory program, basal insulin control program, corrective insulin control program, and other program(s) respectively). The counter-regulatory controller 22 generates a counter-regulatory dose control signal 34 provided to a counter-regulatory agent delivery device 14-1. Respective outputs 36-40 from the insulin controllers 24-28 are combined to form an overall insulin dose control signal 42 provided to insulin delivery device(s) 14-2. The insulin delivery device(s) 14-2 may include devices tailored to deliver different types and/or quantities of insulin, with the exact configuration being known to and under the control of the controllers 24-28. For ease of description the collection of one or more insulin delivery devices 14-2 is referred below to in the singular as an insulin delivery device 14-2.

Also shown in FIG. 2 are other input/output signals of the various controllers, including the glucose level signal 19 and parameters 20 as well as a set of inter-controller signals 44. The inter-controller signals 44 enable communication of information from one controller, where the information is developed or generated, to another controller where the information is used for that controller's control function. Details are provided in the description of the control functions below.

The corrective insulin controller 26 is the primary dynamic regulator of blood glucose level. It may use any of a variety of control schemes, including for example an MPC cost function in a manner described in US patent publication 2008/0208113A1, the contents of which are incorporated by reference herein. In some embodiments a counter-regulatory agent may not be present or may not be used, in which case the counter-regulatory controller 22 may be absent. However, as described below, in one scheme the counter-regulator controller 22 is still present and still generates values of doses of the counter-regulatory agent as information for use by the corrective insulin controller 26, even though no counter-regulatory agent is actually delivered. This includes situations where the counter-regulatory agent is absent or unavailable or inaccessible for delivery, or the counter-regulatory agent delivery device 14-1 is absent or unavailable or inaccessible for performing the delivery, or both, and whether such situations arise on a temporary, permanent, or intermittent basis.

Figure 3:
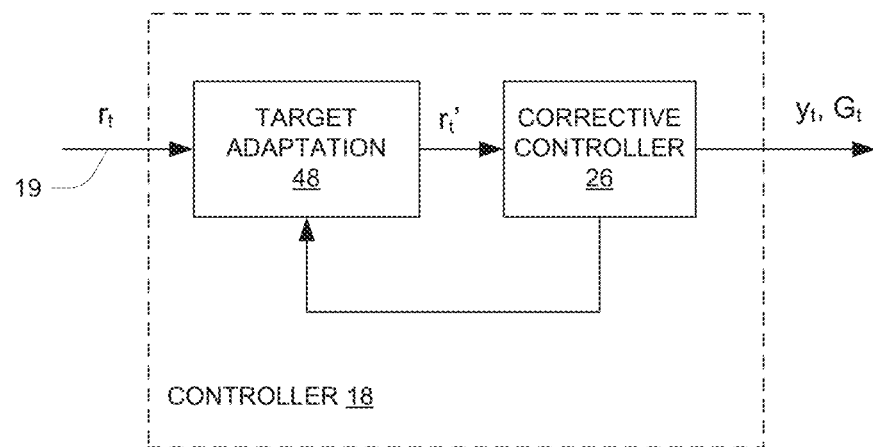
FIG. 3 is a block diagram of a corrective insulin controller.

FIG. 3 shows the controller 18 in additional detail, according to one embodiment. It includes the corrective controller 26 as well as target adaptation 48. The corrective controller 26 carries out the dynamic regulation of glucose level based on an input target glucose level shown as $r_t'$. This dynamic value is generated by the target adaptation 48 partly on the basis of the input (generally fixed) target glucose level signal $r_t$. In other embodiments, the target adaptation 46 may be in a separate controller (e.g., one of the other controllers 28 of FIG. 2). The dynamic target value may be used by only one or by multiple of the controllers within controller 18.

Figure 4:
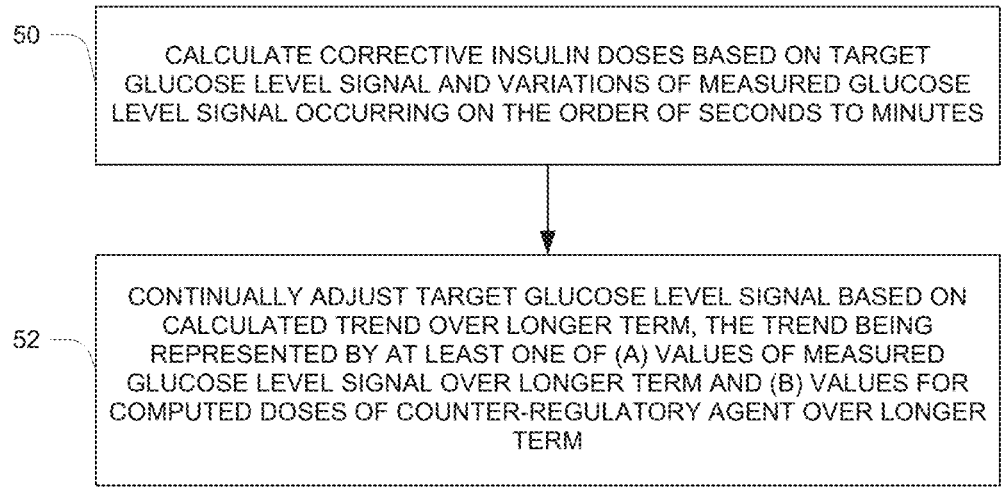
FIG. 4 is a flow diagram of high-level operation of the blood glucose level controller with respect to adjusting target glucose level.

FIG. 4 illustrates certain operation pertaining to the controller 18 at a high level. Generally it continually calculates an insulin dose control signal (e.g., insulin dose control signal 38) in response to (a) a measured glucose level signal (e.g., glucose level signal 19) and (b) a target glucose level signal, a specific example of which is described below. In doing so, at 50 it calculates corrective insulin doses based on the current (latest) target glucose level signal and variations of the measured glucose level signal occurring on the order of seconds to minutes. This is the function of the corrective control 46 of FIG. 3. At 52, the corrective insulin controller 26 continually adjusts the target glucose level signal based on a calculated trend over a longer term of at least one of (a) values of the measured glucose level signal over the longer term and (b) values for computed doses of a counter-regulatory agent over the longer term. This is the function of the target adaptation 48 of FIG. 3.

Example

A specific example is provided to illustrate the above.

Using $r_t$ to represent the input or "raw" target glucose level signal 19, and $r_t'$ to represent the dynamic target glucose level signal that is used by the corrective controller 26 and counter-regulatory controller 22, then one implementation of the target adaptation method is:

$$r_t' = r_t + f(G_t) + f(y_t), r_L \leq r_t' \leq r_H, \quad (1)$$

where $G_t$ are computed (intended) doses of a counter-regulatory agent (e.g. glucagon or glucose/dextrose), $f(G_t)$ is some function of $G_t$, $f(y_t)$ is some function of the glucose level $y_t$, and $r_L$ and $r_H$ are predetermined lower and upper bounds on $r_t'$ (which could themselves be dynamic). As an example, $f(G_t)$ could be given by $$f(G_t) = \sum_{k=t-N}^{t} S_k^{G_k} G_k, \quad (2)$$

where N defines the length of an interval over which accumulation (summation) of $G_t$ is performed, and $S_t^{G_t}$ is a scaling or gain factor that defines the magnitudes of the offsets caused on $r_t'$ by each contribution from $G_t$ included in the summation. The scaling or gain factor $S_t^{G_t}$ could vary depending only on the temporal position of contributions of $G_t$ (e.g. linearly, non-linearly, piecewise, etc.), i.e., $S_t^{G_t} = S_t$, or depending only on the magnitude of contributions of $G_t$ (e.g. linearly, non-linearly, piecewise, etc.), i.e.. $S_t^{G_t} = S^{G_t}$, or both, or neither by potentially being constant for all contributions. On the other hand, $f(y_t)$ could be given by $$f(y_t) = \sum_{k=t-N}^{t} S_k^{y_k} y_k, \quad (3)$$

where, similarly, $S_t^{y_t}$ is a scaling or gain factor that defines the magnitudes of the offsets caused on $r_t'$ by each contribution from $y_t$ included in the summation. The scaling or gain factor $S_t^{y_t}$ could take on similar dependencies to those described for $S_t^{G_t}$. One practical implementation includes $S_t^{y_t}$ being relatively low (or 0) for high values of $y_t$ and progressively higher for lower values of $y_t$, both assessed relative to $r_t$ and/or a relevant physiological range (e.g. 70-120 mg/dl). Note that although both Eq. (2) and Eq. (3) are formulated in discrete time, counterpart continuous-time integration formulations are an obvious variant for implementing the described method.

In one embodiment the computed quantity associated with a counter-regulatory agent may still be present even in systems where the counter-regulatory agent is completely absent, such as in insulin-only systems, by basing the implementation on a signal representing the intended counter-regulatory delivery had it been possible. This similarly applies when the counter-regulatory agent is temporarily absent in a multi-hormonal system, such as during periods when the counter-regulatory agent or its delivery channel become unavailable or delivery of the counter-regulatory agent via its channel becomes not possible for whatever reasons.

Figure 5:
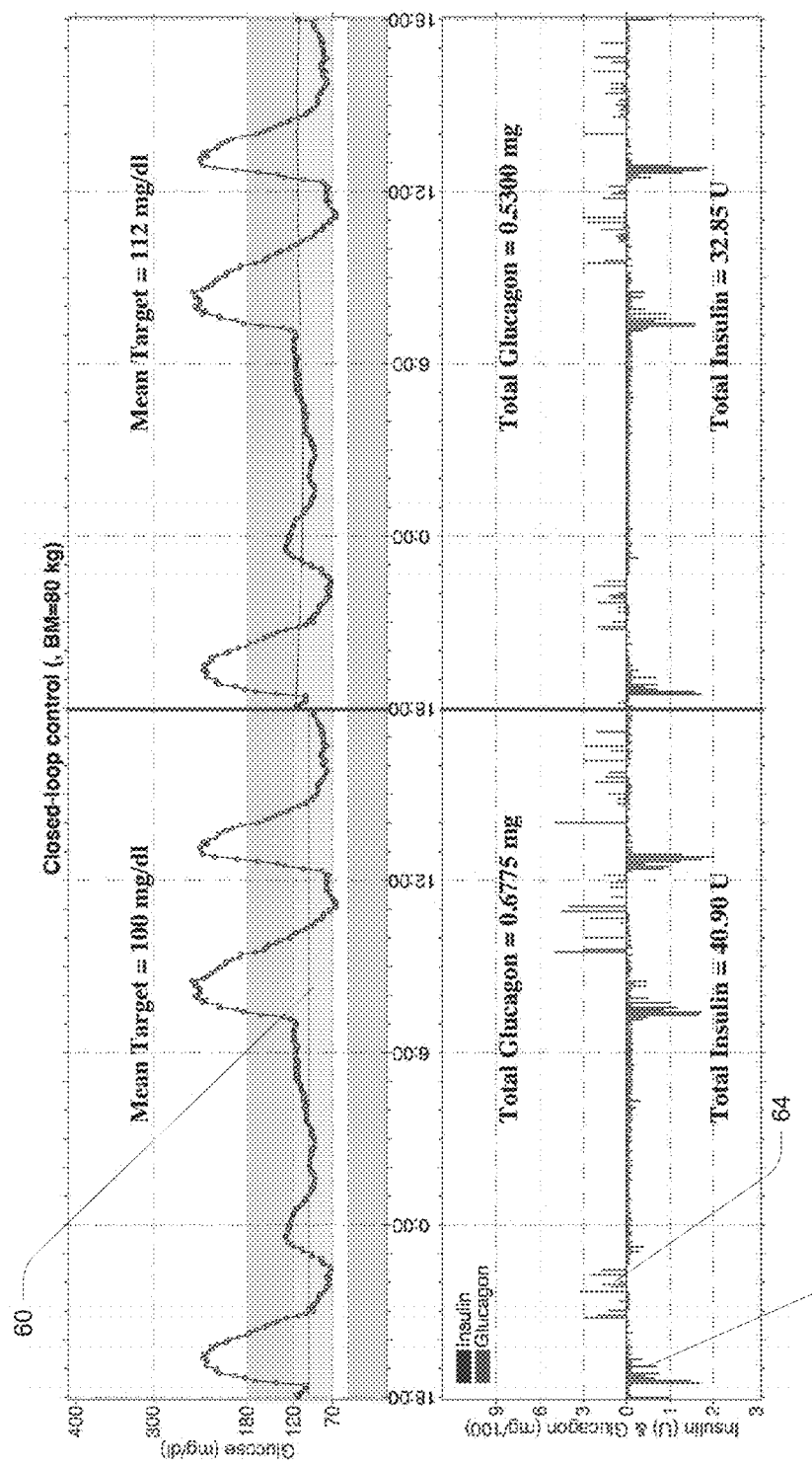
FIGS. 5 and 6 are plots of results of simulations of the disclosed operation.
Figure 6:
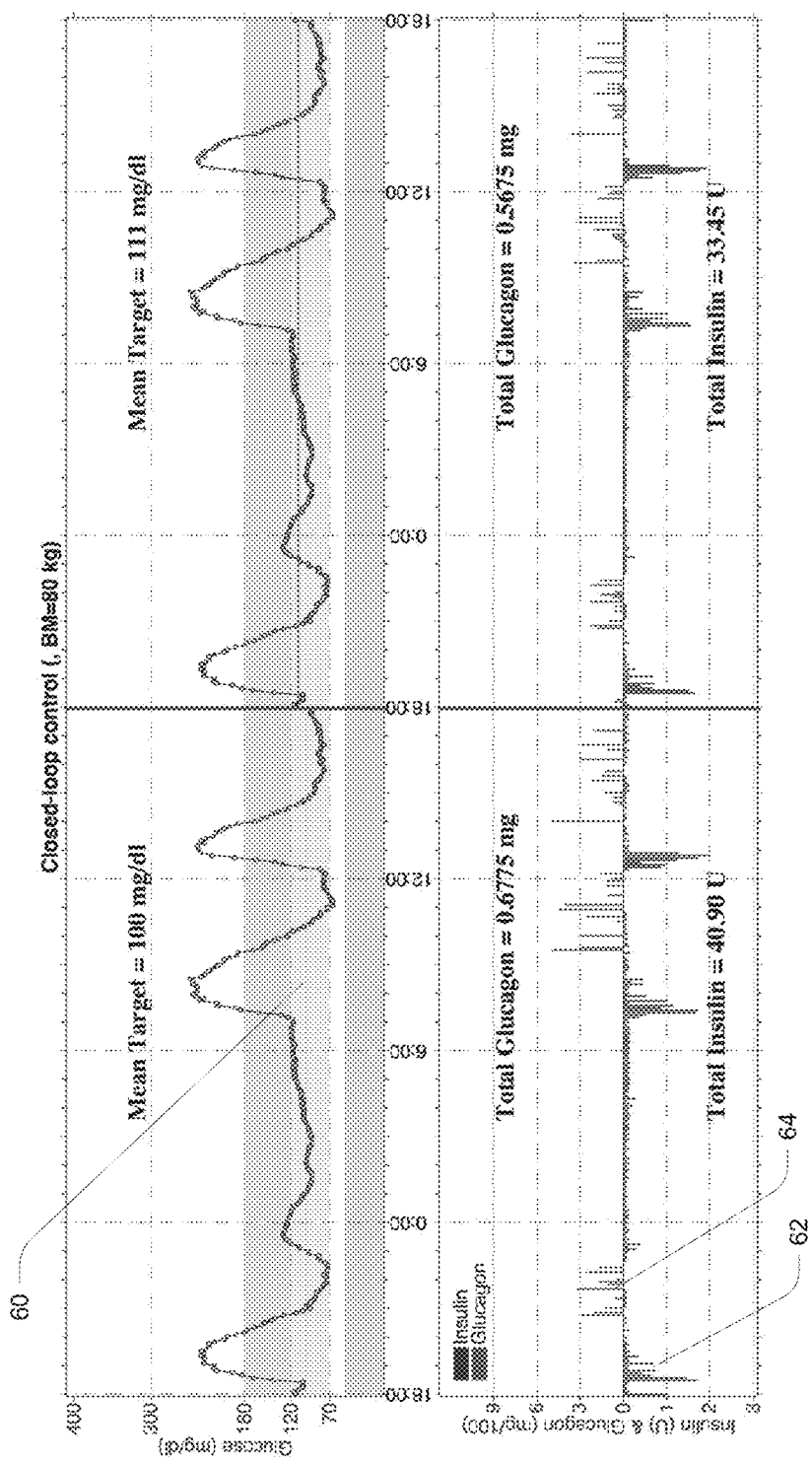

FIGS. 5 and 6 present results of simulations demonstrating the described method. Both plots show 48-hour simulations using the same recurring 24-hour continuous glucose monitoring (CGM) trace. In both simulations, the first 24-hour period uses the same closed-loop algorithm without the implementation of the described method and using a constant glucose target $r_t$ of 100 mg/dl, whereas the second 24-hour periods use the same algorithm with the implementation of Eq. (1), with $r_t$=100 mg/dl, [$r_L$: $r_H$]=[100; 150] mg/dl, and N corresponding to one day. Generally, N will cover a longer term than the much shorter term (seconds to minutes) over which corrections could be made by the corrective insulin controller 26. In these plots, the glucose target is plotted as a trace 60 spanning across the upper panel of the graph. Calculated insulin doses are shown at 62 as extending downward, while calculated glucagon doses are shown at 64 as extending upward. Both simulations assume a bihormonal configuration, although the implementation may be the same in the insulin-only configuration where the counter-regulatory agent is absent.

FIG. 5 presents results of a first simulation A, with $S_t^{y_t} \equiv 0$ in Eq. (3) and with $$S_t^{G_t} \equiv S,$$

(i.e. a constant relative to time t and values of $G_t$) in Eq. (2).

FIG. 6 presents results of a second simulation B, with $S_t^{G_t} \equiv 0$ in Eq. (2), and $$S_t^{y_t} = S^{y_t}, \forall y_t < 100 \text{ mg/dl},$$

$$S_t^{y_t} = 0, \forall y_t \geq 100 \text{ mg/dl},$$

(i.e. $S_t^{y_t}$ is constant relative to time but with dependence on $y_t$) in Eq. (3).

Relevant results from the two simulations are summarized in Table 1. In both simulations, the control system issued 40.90 U of insulin and 0.6775 mg of glucagon in the first 24 hours. In the second 24-hour period in simulation A (FIG. 5) the issued dosing was reduced to 32.85 U for insulin and 0.53 mg for glucagon, and the dynamic target glucose $r_t'$ floated around a mean of 112 mg/dl. In the second 24-hour period in simulation B (FIG. 6), the issued dosing was reduced to 33.45 U for insulin and 0.5675 mg for glucagon, and the dynamic target glucose $r_t'$ floated at 111 mg/dl. Thus these simulations demonstrate desirable reductions in total administered insulin over a period while achieving essentially the same control effect over that period.

TABLE 1

Relevant results from simulations A and B of FIGS. 5 and 6.

| | Simulation A, First 24 h | FIG. 5 Second 24 h | Simulation B, First 24 h | FIG. 6 Second 24 h |
| --- | --- | --- | --- | --- |
| Mean Target, mg/dl | 100 | 112 | 100 | 111 |
| Insulin, U | 40.90 | 32.85 | 40.90 | 33.45 |
| Glucagon, mg | 0.6775 | 0.5300 | 0.6775 | 0.5675 |

A glucose-control system is disclosed that employs an adaptive (dynamic) glucose target, including when the target is a single glucose level value or when it represents a range or interval of glucose levels. The adaptation of the glucose target may be autonomous in accordance with some mathematical formulation. The adaptive glucose target may be constrained to remain within predefined upper and lower bounds.

The adaptation of the glucose target may be for the purpose of limiting the frequency, duration, or severity of low or near low glucose levels (such as below or near the low end of normal range) in order to provide safer and/or more stable glucose control.

The adaptation of the glucose target may be for the purpose of maintaining an achieved mean glucose over a period of time to within a range of mean glucose values in order to minimize the long-term complications of diabetes, preferably avoiding a mean glucose level any lower than what is necessary to reduce long-term complications of diabetes.

The adaptation of the glucose target may be for the purpose of modulating or limiting the actual delivery of or just computation of (hypothetical) doses of a counter-regulatory agent to insulin in order to provide safer and/or more stable glucose control. It may alternatively be for the purpose of modulating or limiting the delivery of insulin in order to provide safer and/or more stable glucose control.

The adaptation of the glucose target may be based on the glucose levels in a past and/or receding time horizon, and it may be based on glucose levels that fall below a certain threshold in a past and/or receding time horizon.

The adaptation of the glucose target may be based on actual delivery of or just computation of (hypothetical) doses of a counter-regulatory agent over a past and/or receding time horizon.

The adaptation of the glucose target may be part of a glucose-control system that employs the delivery of only insulin, or alternatively employs the delivery of insulin and a counter-regulatory agent or agents, or alternatively that employs the delivery of insulin, a counter-regulatory agent or agents, and potentially other agents.

The adaptation of the glucose target may coexist with an option for the user to set a static glucose target on a temporary (including isolated, recurring, or scheduled) basis. The glucose control system may be autonomous or semi-autonomous, and the adaptation of the glucose target may be different depending on whether the counter-regulatory agent is actually delivered or is computed but not actually delivered.

The disclosed adaptation technique may be used in a variety of types of automatic glucose control system. In one example, it may be used in a glucose control system such as disclosed in U.S. Pat. No. 7,806,854 or PCT International Publication No. WO 2012/058694 A2.

While various embodiments of the invention have been particularly shown and described, it will be understood by those skilled in the art that various changes in form and details may be made therein without departing from the scope of the invention as defined by the appended claims.

What is claimed is:

1. A method of operating a glucose control system having an input/output interface configured to receive a measured glucose level signal indicative of a measured glucose level of a subject from a glucose sensor and to transmit a dose control signal to a delivery device configured to deliver doses of at least one glucose control agent for infusion into the subject, the method comprising:

by an electronic processor of the glucose control system configured to execute a control scheme to generate the dose control signal in response to (a) the measured glucose level signal and (b) a target glucose level signal, wherein the electronic processor is configured to execute specific computer-executable instructions stored in a non-transitory memory connected to the electronic processor:

calculating corrective doses of the at least one glucose control agent based on a target glucose level signal and variations of the glucose level signal occurring over a correction dose period on the order of seconds to minutes;

calculating an adapted value of the target glucose level signal based at least on a function of the glucose level signal over at least a portion of a target glucose level calculation period that is longer than the correction dose period, wherein the function is a weighted sum using a scaling factor with which measured glucose levels are multiplied to determine offsets caused on the adapted value of the target glucose level signal by respective contributions from measured glucose levels of the subject, and wherein the scaling factor varies depending on the respective measured glucose levels of the subject; and generating the dose control signal to cause delivery of corrective doses calculated using the adapted value of the target glucose level signal, wherein the glucose control agent comprises at least one of insulin or an insulin analog.

2. The method of claim 1, wherein generating the dose control signal to cause delivery of the corrective doses calculated using the adapted value of the target glucose level signal reduces total administered insulin or insulin analog while achieving essentially the same glucose control effect during the correction dose period compared to a period during which a constant value of the target glucose level signal is used to generate the dose control signal.

3. The method of claim 1, wherein calculating the adapted value of the target glucose level signal comprises calculating the adapted value of the target glucose level signal from a static target glucose level signal provided as an input parameter to the electronic processor.

4. The method of claim 1, wherein calculating the adapted value of the target glucose level signal is based on a second calculated longer-term trend represented by at least values for computed doses of a counter-regulatory agent over the target glucose level calculation period.

5. The method of claim 4, wherein the glucose control system further includes a counter-regulatory agent delivery device operative in response to a counter-regulatory dose control signal to deliver doses of a counter-regulatory agent for infusion into the subject.

6. The method of claim 5, further including, by the electronic processor, generating the counter-regulatory agent dose control signal in response to the measured glucose level signal and the target glucose level signal to maintain euglycemia of the subject.

7. The method of claim 1, wherein the scaling factor varies depending on a temporal position of contributions of the respective measured glucose levels.

8. The method of claim 1, wherein the scaling factor is a relatively low value for high values of measured glucose level and progressively higher for lower values of measured glucose level.

9. The method of claim 1, wherein the function for calculating the adjusted value of the target glucose level signal is based on at least computed doses of a counter-regulatory agent over a past and/or receding period.

10. The method of claim 9, wherein the function is a weighted sum using a further scaling factor that defines magnitudes of offsets caused on the target glucose level signal by respective contributions from the computed doses of the counter-regulatory agent.

11. The method of claim 10, wherein the further scaling factor varies depending on a temporal position of contributions of the respective computed doses of the counter-regulatory agent.

12. The method of claim 10, wherein the further scaling factor varies depending on contributions of the respective computed doses of the counter-regulatory agent.

13. The method of claim 10, wherein the glucose control system further includes a counter-regulatory agent delivery device operative in response to a counter-regulatory dose control signal to deliver doses of the counter-regulatory agent for infusion into the subject.

14. The method of claim 10, wherein the counter-regulatory agent is not infused into the subject, and wherein the computed doses of the counter-regulatory agent represent doses that would be infused into the subject if the counter-regulatory agent were being infused into the subject.

15. The method of claim 1, wherein a past and/or receding time horizon is applied to measured glucose levels.

16. The method of claim 1, wherein thresholding is applied to the measured glucose levels for inclusion in the past and/or receding time horizon.

17. The method of claim 1, further including, by the electronic processor, accepting user input for inhibiting or overriding glucose adaptation by setting a static glucose target on a temporary basis.

18. The method of claim 1, operable in both a fully autonomous manner and a semi-autonomous manner.

19. The method of claim 1, wherein calculating the adjusted value of the target glucose level signal is invoked on a time-scale that is on the same time scale or coinciding with the time scale used for obtaining values of the measured glucose level signal, or with a shorter or longer time scale than the time scale used for obtaining values of the measured glucose level signal.

* * * * *